United States Patent
Labsky et al.

[11] 3,950,399
[45] Apr. 13, 1976

[54] 1,4-DIACYLOXY-2,3-BUTENDIOL

[75] Inventors: Jiri Labsky; Josef Exner, both of Prague, Czechoslovakia

[73] Assignee: Ceskoslovenska akademie ved, Prague, Czechoslovakia

[22] Filed: Jan. 30, 1974

[21] Appl. No.: 438,010

[30] Foreign Application Priority Data
Feb. 23, 1973   Czechoslovakia................. 1315-73

[52] U.S. Cl...... 260/486 R; 260/89.5 R; 260/486 B
[51] Int. Cl.² ........................................ C07C 69/54
[58] Field of Search ..................... 260/486 B, 486 R

[56] References Cited
UNITED STATES PATENTS

| | | | |
|---|---|---|---|
| 2,484,487 | 10/1949 | Caldwell.......................... | 260/486 B |
| 3,373,075 | 5/1968 | Fekete et al. ................... | 260/486 B |
| 3,676,398 | 7/1972 | D'Alelio.......................... | 260/486 B |

*Primary Examiner*—Lorraine A. Weinberger
*Assistant Examiner*—P. J. Killos
*Attorney, Agent, or Firm*—Murray Schaffer

[57] ABSTRACT

A new compound, 1,4-diacyloxy-2,3-butanediol, having the general formula

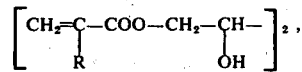

where R is hydrogen atom or methyl group. The compound can be used above all as a crosslinking agent in the preparation of crosslinked hydrophilic polymeric gels. This compound can be prepared by opening the epoxy ring in such a way, that 1 mole of 1,2-3,4-diepoxybutane is treated with 2 moles of unsaturated acid of the general formula

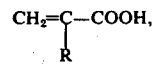

where R has the aforementioned meaning.

1 Claim, No Drawings

1,4-DIACYLOXY-2,3-BUTENDIOL

The invention relates to 1,4-diacyloxy-2,3-butanediol and to a method for its production.

In the preparation of hydrophilic crosslinked polymeric gels, a crosslinking agent should advantageously contain hydrophilic groups, to prevent the gel properties from undesirable changes caused by increasing the agent concentration. Esters of unsaturated acids which carry free hydroxy groups at defined places of the molecule can be prepared only with difficulties, e.g. by acylation of alcoholic sugars. Complicated mixtures arise in most cases and the isolation of pure individual compounds can be carried out with great difficulty.

The objective of this invention is 1,4-diacyloxy-2,3-butanediol of the general formula I

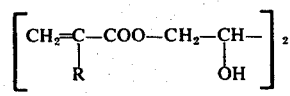 (1)

where R is hydrogen atom or methyl group.

This compound can be prepared by opening the epoxide ring in the way, that 1 mole of 1,2-3,4-diepoxybutane is treated with 2 moles of the unsaturated acid having the general formula II

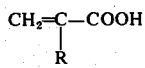 (II)

where R has the above given meaning.

The reaction can be advantageously carried out in the presence of a tertiary base, for instance triethylamine, and at the temperatures 0° to 100°C, preferably 50° to 80°C.

The most simple compound of this group is the dimer of hydroxyethyl acrylate or methacrylate (R = H and CH₃, respectively), which represents the very suitable and easily accessible crosslinking agent. As this monomer is crystalline, it can be readily prepared in a pure form.

The compounds of the general formula I are advantageously used as crosslinking agents in the preparation of hydrophilic polymeric gels because they do not suppress hydrophilicity of the polymer.

The invention is further illustrated in EXAMPLES of performance.

EXAMPLE 1

A mixture consisting of 22.2 g of 1,2-3,4-diepoxybutane, 50 g of methacrylic acid, 0.2 g of triethylamine and 0.05 g of hydroquinone was heated to 70°C for 9 hours. The reaction mixture was dissolved in 500 ml of ether and shaken with water (100 ml), aqueous sodium bicarbonate and water. The etherous solution was then dried over molecular sieve A4. The product crystallized out after evaporation of ether and may be recrystallized from hexane; m.p. 53°–55°C, the yield was 8 g.

EXAMPLE 2

A mixture consisting of 6 g of 1,2-3,4-diepoxybutane, 15 g of methacrylic acid, 0.1 g of triethylamine and 0.1 g of hydroquinone was heated to 50°C for 20 hours. The resulting compound crystallized after seeding. The crystals were sucked off and twice recrystallized from hexane; the yield was 1 g, m.p. 54°C.

We claim:
1. 1,4-Diacyloxy-2,3-butanediol of the general formula I

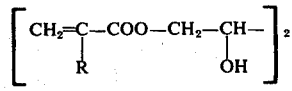 (I)

where R is a hydrogen atom or methyl group.

* * * * *

UNITED STATES PATENT OFFICE
CERTIFICATE OF CORRECTION

Patent No. 3,950,399     Dated April 13, 1976

Inventor(s) JOHANNES KECK, KLAUS-REINHOLD NOLL, HELMUT PIEPER GERD KRUGER and SIGFRID PUSCHMANN It is certified that error appears in the above-identified patent and that said Letters Patent are hereby corrected as shown below:

Col. 4, line 27, second occurrence "or" should read -- of --

Col. 5, line 68     "corresponding" should read -- corresponding --

Col. 23, line 17     "dihydrocchloride" should read -- dihydrochloride --

Col. 24, line 66     "hexametylenea-" should read -- hexamethylenea- --

Col. 25, line 6     "hydrochloride" should read -- dihydrochloride --

Col. 34, line 1     "<190°C" should read -- >190°C --

Col. 34, line 9     "<190°C" should read -- >190°C --

Col. 36, line 25     "<275°C" should read -- >275°C --

Col. 43, line 28     "<121°C" should read -- >121°C --

Col. 45, line 12     "<70°C" should read -- >70°C --

Col. 46, line 28     "<61°C" should read -- >61°C --

Signed and Sealed this

Sixth Day of July 1976

[SEAL]

Attest:

RUTH C. MASON  
Attesting Officer

C. MARSHALL DANN  
Commissioner of Patents and Trademarks